United States Patent [19]
Knollmueller

[11] 3,992,429
[45] Nov. 16, 1976

[54] ALKOXYSILANE MULTIPLE CLUSTER COMPOUNDS AND THEIR PREPARATION

[75] Inventor: Karl O. Knollmueller, Hamden, Conn.

[73] Assignee: Olin Corporation, New Haven, Conn.

[22] Filed: Mar. 24, 1976

[21] Appl. No.: 669,714

[52] U.S. Cl. .......................... 260/448.8 A; 252/78.3
[51] Int. Cl.² .......................... C07F 7/04; C07F 7/18
[58] Field of Search ........................... 260/448.8 A

[56] References Cited
UNITED STATES PATENTS 2,711,418  6/1955  Kather .......................... 260/448.8 A
2,727,054  12/1955  Wright .......................... 260/448.8 A Primary Examiner—Paul F. Shaver
Attorney, Agent, or Firm—F. A. Iskander; T. P. O'Day

[57] ABSTRACT

Novel alkoxysilane cluster compounds are described having the formula $$M\{OSi[OSi(OR')_3\}_a$$

or $$M\{OSiR[OSi(OR')_3]_2\}_a$$

wherein $a = 2$, 3 or 4; M is a substituted or unsubstituted branched or straight chain hydrocarbon di-, tri- or tetraradical having up to 25 carbon atoms; R is hydrogen, an alkyl, alkenyl, aryl or aralkyl group and each R' is independently selected from the same group as R with the proviso that at least a majority of R' radicals are sterically hindered alkyl groups having at least 3 carbon atoms. The preparation of these novel alkoxysilane cluster compounds is also described.

19 Claims, No Drawings

ALKOXYSILANE MULTIPLE CLUSTER COMPOUNDS AND THEIR PREPARATION

Silicate esters, silanes and oxysilanes are well known for their utility as functional fluids and many of these compounds have been proposed for use as heat transfer fluids, hydraulic fluids, brake fluids, transmission fluids, and the like. Among these silicon-containing compounds of particular interest in the functional fluid fields are various oxysilane compounds which contain hydrocarbon units, e.g., alkylene and oxyalkylene units, such as are described, for example, in U.S. Pat. Nos. 3,361,714; 3,723,491; 3,865,859 and 3,887,601. Novel alkoxysilane compounds containing hydrocarbon units and exhibiting desirable functional fluid properties have now been discovered which have heretofore not been described in the literature.

Thus, the present invention is directed to unique alkoxysilane compounds and their preparation. More particularly, the present invention is directed to novel alkoxysilane multiple cluster compounds, and their preparation, the compounds being those having the general formulas:

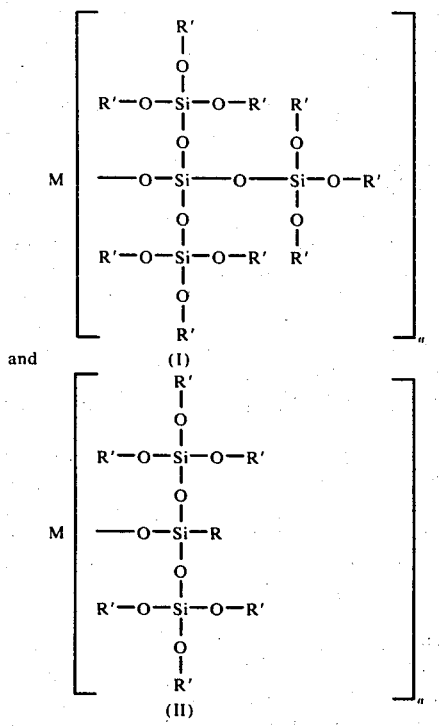

wherein $a = 2$, 3 or 4; M is a substituted or unsubstituted branched or straight chain hydrocarbon di-, tri- or tetraradical having up to 25 carbon atoms; R is hydrogen, an alkyl, alkenyl, aryl or aralkyl groups and each R' is independently selected from the same group as R with the proviso that at least a majority of R' radicals are sterically hindered alkyl groups having at least 3 carbon atoms.

The above formulas (I) and (II) may be written in abbreviated form as follows:

$$M\{OSi[OSi(OR')_3]_3\}_n \qquad (III)$$

and $$M\{OSiR[OSi(OR')_3]_2\}_n \qquad (IV)$$

wherein the variables are defined above.

The compounds of the present invention are those represented by the above formulas wherein $a = 2$, 3 or 4, as mentioned. Desirably, $a = 2$ or 3 and preferably $a = 2$. The substituent M is defined as a substituted or unsubstituted hydrocarbon radical, either branched or straight chained and branched radicals are preferred. By hydrocarbon radical is meant both oxylated radicals and radicals which have not been oxylated. Thus, M may be a straight or branched chain hydrocarbon diradical, triradical or tetraradical containing carbon and hydrogen atoms, with or without inert substituents. Alternatively, M may be a straight or branched chain hydrocarbon diradical, triradical or tetraradical having one or more ether and/or ester units, with or without inert substituents. The radical M is a hydrocarbon radical, as defined, having up to about 25 carbon atoms, desirably having about 2 to about 18 carbon atoms, and preferably having about 4 to about 12 carbon atoms. The hydrocarbon radical may, as mentioned, be unsubstituted or it may be substituted and these substituents include, e.g., hydroxy groups, phenyl groups and any substituents which do not interfere with the hydrolytic stability of the molecule to an undesirable degree.

R is defined as hydrogen, an alkyl, alkenyl, or aryl or aralkyl radical. Desirably, R is hydrogen, an alkyl or alkenyl having about 1 to about 18 carbon atoms or an aryl or aralkyl having about 6 to about 24 carbon atoms. Preferably, R is hydrogen, an alkyl having about 1 to about 8 carbon atoms or an aryl or aralkyl having about 6 to about 14 carbon atoms. In the above formulas, each R' is independently selected from the same group as R, with the proviso that at least a majority of the R' radicals are sterically hindered alkyl groups having at least 3 carbon atoms. The desired and preferred groups for R' are the same as for R subject to the preceding proviso. Desirably, at least a majority of the R' radicals are sterically hindered alkyl groups having about 3 to about 24 carbon atoms and preferably are sterically hindered alkyl groups having about 4 to about 12 carbon atoms. By sterically hindered alkyl groups is meant alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered alkyl groups include sec. butyl, isobutyl, 2-ethyl butyl, 2-ethyl pentyl, 3-ethyl pentyl, 2-ethyl hexyl, 3-ethyl hexyl, and 2,4-dimethyl-3-pentyl, etc.

In the method of preparing the novel alkoxysilane cluster compounds of the present invention a halogenated oxysilane compound is reacted with a polyol in the presence of a hydrogen halide acceptor base, and optionally a solvent, to obtain a cluster compound-containing product.

The halogenated oxysilane compound used in the method of preparing the cluster compounds of the present invention are those having the formulas:

$$XSi[OSi(OR')_3]_3 \qquad (V)$$

and $$XSiR[OSi(OR')_3]_2 \qquad (VI)$$

wherein R and R' are defined above and each X is a halogen selected from F, Cl, Br and I, preferably from Cl, Br and I, especially Cl. The compound represented by Formula (V) above is obtained by reacting a trihalosilane with a trialkoxysilanol in the presence of an acid acceptor. This is more fully set forth in copending U.S. patent application Ser. No. 616,437, entitled "Halogenated Alkoxysilane Intermediate Compounds and Their Preparation," filed on Sept. 24, 1975, by the present inventor, and incorporated herein by reference. The compound of Formula (VI) above is prepared in the same manner except that a silicon tetrahalide is used in place of the trihalosilane in the reaction.

In preparing the cluster compounds of the present invention, the halogenated oxysilane compounds of Formulas (V) and (VI) above are reacted with a polyol which is represented by the formula:

wherein M and $a$ are defined above. Thus, the polyol starting materials may be difunctional, trifunctional or tetrafunctional, and include diols such as ethylene glycol, propylene glycol, polyethylene glycol ethers, neopentyl glycol, and 2 ethyl 1,3 hexane diol. Also included are triols, e.g., trimethylolpropane, and tetrols, e.g. pentaerythitol.

The halogenated oxysilane compound and the polyol are reacted in the presence of a hydrogen halide acceptor base compound. The acceptor may be any compound which will accept hydrogen halide and thereby promote the formation of the cluster compounds of the present invention pursuant to Equations (A) and (B) shown below. Among the preferred acceptors are the nitrogenated tertiary organic base compounds having at least 3 carbon atoms, e.g., the lower alkyl and aryl tertiary amines such as triethyl amine, tributyl amine, as well as pyridine, substituted pyridine, N,N'-dimethyl-aniline, etc.

The formation of the novel cluster compounds of the present invention using the above reactants may be represented by the following two equations:

When the halogenated oxysilane compound represented by Formula (V) above is used, the cluster compound of Formula (III) is obtained:

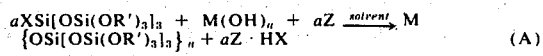

wherein Z is the hydrogen halide acceptor base and the other reactants are described above.

When the halogenated oxysilane compound represented by Formula (VI) above is used, the cluster compound of Formula (IV) is obtained:

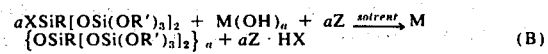

Equations (A) and (B) suggest that the principal reaction in the method of preparing the cluster compounds of the present invention be carried out in a solvent. While the solvent is not necessary, it does serve to moderate the rate of reaction and thereby to enhance the separation of the acceptor Z-hydrogen halide HX from the cluster compound product. The solvent used may be any nonprotonic solvent which dissolves the reactants and does not interfere with the Equation (A) or Equation (B) reaction. Among the solvents which may be used are benzene, toluene, xylene, high boiling petroleum ether, other ethers such as tetrahydrofurane, dioxane, and the like.

In general, about a stoichiometric amount or a slight excess of the stoichiometric amount of halogenated oxysilane compound over the polyol is employed to enhance the formation of the cluster compounds of the present invention and to promote completion of the desired reaction. Thus about 0.5 moles to about 3 moles or more of the halogenated oxysilane compound is used per equivalent of polyol and preferably at least about 1 mole to about 1.5 moles of the halogenated oxysilane compound is used. By equivalent is meant equivalent number of OH groups which is desired to be displaced. The total solvent used in the reaction is a matter of choice and not critical to the reaction, although good results are achieved when about 5 moles to about 50 moles, and preferably about 10 to about 30 moles of solvent is used per mole of halogenated oxysilane compound. In general, when the solvent is used, about 0.5 to about 10 parts of solvent per part by weight of total reactants, and preferably about 1 to about 5 parts of solvent per part by weight of total reactants may be used. The hydrogen halide acceptor base is advantageously used in stoichiometric amount based on the amount of halogenated oxysilane compound used. In general, about 0.7 to about 5 moles, and preferably about 0.9 to about 1.5 moles of the acceptor is used per mole of halogenated oxysilane compound.

The reaction represented by Equations (A) and (B) may be performed at very low temperatures, room temperature, or even very high temperatures as long as there is no detrimental effect on the reactants or products. Thus the reaction may be carried out at −30° C. up to the reflux temperature of the lowest boiling constituent, and it is preferably carried out at about 0° C. to about 100° C. In a preferred batch method embodiment, the reaction is started at a lower temperature, e.g., between −10° C. and 20° C., and is completed at a higher temperature to drive the reaction as far as possible to completion. Of course, a continuous operation may be employed with a series of reactors in which the first reactor is maintained at the lower temperature and each subsequent reactor is incrementally higher in temperature to drive the reaction to completion. In any event, the cluster compounds are separated from the product mixture by filtrations, distillations or other conventional separation techniques, and the particular separation system chosen merely depends upon the desired purity of the final product and its ultimate utility.

The novel cluster compounds obtained by the method of the present invention are those represented by Formulas (I) through (IV) above and contain an adequate number of silicon atoms to produce good lubricating properties without the need to add lubricity improvers. Additionally, the silicon atoms are adequately shielded by the significant number of sterically hindered alkyl groups having at least 3 carbon atoms and this assures protection against attack by water. Thus, the novel cluster compounds of the present invention have been found to have good hydrolytic stability, good lubricating properties, and low ASTM viscosity indices with many having pour points below −40° C. The novel cluster compounds exhibit these properties both in substantially pure form and in unpurified mixtures with side reaction products obtained by the reactions set forth in Equations (A) and (B) above.

The following examples illustrate various embodiments of the present invention, but the present invention should not be construed to be limited thereto:

EXAMPLE 1

A 1 liter three-neck flask, equipped with a stirrer, thermometer, reflux condenser and an equilibrated dropping funnel is charged with 139 g

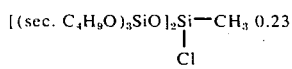

moles in 380 ml benzene. The dropping funnel is charged with a solution of 7.13 g ethylene glycol (0.115 mole) 29.3 g pyridine (0.37 moles) and 35 ml benzene. The addition is carried out at ~30° C., without external cooling the temperature rises to ~40° C. The stirred mixture is subsequently heated to 75°–80° C. for 12 hours. The pyridine hydrochloride is subsequently filtered off whereby 90–98% of the theory is recovered. The rest is removed by washing the benzene solution with water by stirring with 100 ml water for 30 minutes. The organic phase is separated from the water in a separatory funnel, washed Cl$^-$ free and is then dried over CaCl$_2$ or MgSO$_4$. After vacuum stripping of the solvent, ~134 g crude product is obtained. The crude product is fractionated in fractionation apparatus with a Vigreux column, which is heated to prevent heat losses at the high distillation temperatures encountered.

After a forerun of products of incomplete addition b.p. 140°–248°/0.01, the product is obtained boiling at 248° ± 2° C./0.01 mm in 77.3% yield.

$n_D^{25} = 1.4175$

Calc. for Si$_6$C$_{52}$H$_{118}$O$_{18}$ Si 14.04%, C = 52.05%, H = 9.91%.

Found Si 14.11%, C = 52.02%, H = 9.87%.

EXAMPLE 2

Using equipment and procedure as in Example 1, but reacting 52.05 g ClSi [(sec. C$_4$H$_9$O)$_3$SiO]$_3$ = 0.061 mole in 100 ml benzene with a mixture of 1.89 g ethylene glycol 0.035 mole and 10 g pyridine = 0.126 moles affords after the washing and topping off volatile by-products boiling up to 280° C./9 × 10$^{-3}$ mm Hg, 15.75 g clear product with the following analytical data Calc. for Si$_8$C$_{74}$H$_{166}$O$_{26}$ Si 13.24%, C = 52.38%, H = 9.86%.

Found Si 14.1%, C = 51.98%, H = 9.72%.

The fraction boiling at 280°/9 × 10$^{-3}$ mm analyzes as follows:

(3.55 grams)    Si 13.5%, C = 52.28%, H = 9.52%; Total yield 37.4%.

EXAMPLE 3

Following the procedure of Example 1, 125 g ClSi [(sec. C$_4$H$_9$O)$_3$SiO]$_2$, 0.207 mole in 300 ml benzene is reacted with 13.15 g 2 ethyl-1,3 hexane diol (0.103 mole), and 17.65 g pyridine (0.223 moles). After heating for 12 hours to 60°–70° C. and the usual work-up there is obtained 17.4 g of

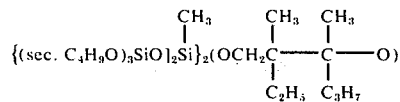

b.p. 256°–260°/10$^{-2}$ mm $n_D^{25} = 1.4254$.

ANALYSIS

Calc. for Si$_6$C$_{58}$H$_{130}$O$_{18}$, Si = 13.23%, C = 54.25%, H = 10.20%.

Found Si = 13.24%, C = 54.11%, H = 10.09%.

EXAMPLE 4

Following the procedure outlined in Example 1, 123.3 g

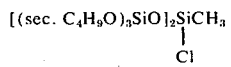

(0.204 mole) in 300 ml benzene is reacted with 10.61 g neopentyl glycol (0.102 mole) and 21 g pyridine (0.265 mole) in 80 ml benzene at 20° C. After heating to 80° C. for 12 hours and the usual work-up, there is obtained:

72.2 g

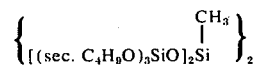

(OCH$_2$)$_2$C(CH$_3$)$_2$ 57% yield b.p. 260–265/~5 × 10$^{-3}$ mm $n_D^{25} = 1.4198$ Calc. C = 53.18%, Found 53.39%, MW 1200 (by VPO).

Calc. H = 10.06%, Found 10.06%, Calc. 1242.

Calc. Si = 13.57%, Found 13.53%,

EXAMPLE 5

Reacting 96.24 g

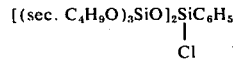

(0.144 moles) with 7.51 g neopentyl glycol (0.072 moles) and 18.04 g pyridine (0.23 moles) in a total of 360 ml benzene affords 65.4 g (C$_6$H$_5$Si [(sec. C$_4$H$_9$O)$_3$SiO]$_2$)$_2$(OCH$_2$)$_2$C(CH$_3$)$_2$ b.p. 272°–275°/3 × 10$^{-2}$ mm Hg $n_d^{25} = 1.4451$ Yield 66.4%

Analysis:

C Calc. 57.14% Found 58.5% MW 1300 (by VPO)

H Calc. 9.45% Found 9.33% Calc. 1366

Si Calc. 12.33% Found 12.11%

EXAMPLE 6

Reaction of

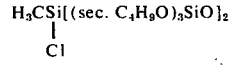

with trimethylolpropane (A23905).

Following the procedure outlined in Example 1, 133.5 g

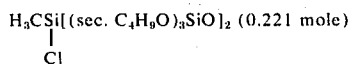

is reacted with 9.87 g $CH_3CH_2C(CH_2OH)_3$ (0.074 mole) and 37.12 g pyridine (0.469 mole) in a total of 380 ml benzene at 25°. The reaction mixture is heated 12 hours to 80° C. After removing the pyridine hydrochloride and the usual work-up there is obtained by fractionation 28.29 g diaddition product

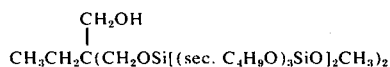

b.p. 248 ± 2°/6 × $10^{-3}$ mm Hg
$n_D^{25}$ 1.4230
and 41.92 g of the desired triaddition product
$H_3C\ CH_2C[CH_2OSi[(sec.\ C_4H_9O)_3SiO]_2CH_3]_3$
b.p. 340°/6 × $10^{-3}$; b.p. 360°/8 = $10^{-2}$ mm
$n_D^{25}$ 1.4252
Analysis:
a. Diaddition Product $C_{56}H_{126}O_{19}Si_6$ Calc. Si 13.25%, C 52.87%, H 9.98% Found Si 13.38%, C 52.81%, H 9.86% MW Calc. 1272 Found 1105 (by VPO)
b. Triaddition Product $C_{81}H_{182}O_{27}Si_9$ Calc. Si 13.73% C 52.84% H 9.96% Found Si 12.74% C 53.03% H 9.98% MW Calc. 1841 Found 1735 (by VPO)

EXAMPLE 7

Reaction of

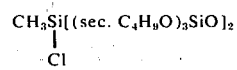

with pentaerythritol.

A reaction flask (three-neck), equipped with stirrer and reflux condenser is charged with 112.2 g

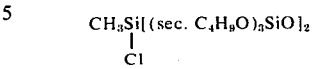

0.185 mole 200 ml toluene and 6.31 g $C(CH_2OH)_4$ (0.0456 mole). 25 g pyridine are added at once and the stirred mixture is heated to reflux. After 6 hours, 40 g more pyridine is added and the heating to ~115° C. is continued for 12 hours. The pyridine hydrochloride formed is dense and is easily removed by filtration. After the usual work-up procedure and removing lower boiling byproducts by fractionation, a product corresponding to the triaddition compound $HOCH-C[CH_2OSi[(sec.\ C_4H_9O)_3SiO]_2CH_3]_3$ is obtained boiling at 295°–300°/0.01 mm
$n_D^{25}$ = 1.4252 45.5 g Analysis: $C_{80}H_{180}O_{28}Si_9$ Calc. Si 13.72 C 52.13 H 9.84 MW 1843 Found Si 14.25 C 52.24 H 9.81 MW about 1700

The products obtained from the above examples are tested for viscosity, wear scar, hydrolysis solids, weight loss and flash point as shown in the following table. The ASTM slope based on viscosity measurements are 100° F. and 210° F. are calculated and used as an indication of change in viscosity in response to temperature changes. The wear scar test is performed with a four ball 40 kg load apparatus at 1800 rpm and 168° F. for 1 hour. The hydrolysis solids test is carried out at 210° F. in the presence of 1/3 weight $H_2O$ and copper metal catalyst for 100 hours. The results establish that the compounds of the present invention are very good functional fluids, as follows:

| | Properties of Multiple Clusters [(sec. $C_4H_9O)_3SiO$] = [OSi ($OC_4H_9$ sec.)$_3$] | | | | | | | |
|---|---|---|---|---|---|---|---|---|
| Example No. | | Pour Print ° F. | Viscosity 100° F. | CS 210° F. | Wear Scar mm (4 Ball, 1800 KPM 1 hr., 40 ky, 167° F.) | Weight Loss 400° F. % | Flask Point ° F. | Hydr. Stability % Solids Formed |
| 1 | $\{[OSi(sec.\ C_4H_9O)_3] \atop H_3CSi \atop [OSi(sec.\ C_4H_9O)_3]\}_2 (OCH_2CH_2O)$ | <−40 | 25.48 | 8.06 | 0.66 | 4.68 | 420 | 0.03 |
| 2 | $\{[(sec.\ C_4H_9O)_3SiO]_3Si\}_2(OCH_2CH_2O)$ | <−40 | 1600 | 214.78 | — | 9.42 | 420 | 0.05 |
| 3 | $\{(sec.\ C_4H_9O)_3SiO]_2Si \atop CH_3\}_2 (OCH_2C(C_2H_5)—C(C_3H_7)—O)$ | <−40 | 49.4 | 11.42 | — | 10.1 | 415 | 0.05 |
| 4 | $\{[(sec.\ C_4H_9O)_3SiO]_2Si \atop CH_3\}_2 (OCH_2C(CH_3)—CH_2O)$ | <−40 | 39.35 | 10.95 | 0.58 | 3.45 | 415 | 0.012 |
| 5 | $\{[OSi(sec.\ C_4H_9O)_3] \atop \bigcirc Si \atop [OSi(sec.\ C_4H_9O)_3]\}_2 (OCH_2C(CH_3)—CH_2O)$ | <−40 | 134.8 | 29.12 | 1.06 | 1.76 | 425 | 0.007 |
| 6a | $CH_3—CH_2 \atop HO—CH_2—C\{(CH_2OSi[OSi(sec.\ C_4H_9O)_3]\}_2$ | <−40 | 38.49 | 9.88 | 0.59 | 5.69 | 280 | — |
| 6b | $CH_3CH_2C\{CH_2OSi[OSi(sec.\ C_4H_9O)_3]_2CH_3\}_3$ | <−40 | 168.69 | 36.61 | 0.6 | 2.76 | 430 | 0.07 |

-continued

Properties of Multiple Clusters [(sec. $C_4H_9O)_3SiO$] = [OSi $(OC_4H_9$ sec.$)_3$].

| Example No. | | Pour Print °F. | Viscosity 100°F. | CS 210°F. | Wear Scar mm (4 Ball, 1800 KPM 1 hr., 40 ky, 167°F.) | Weight Loss 400°F. % | Flask Point °F. | Hydr. Stability % Solids Formed |
|---|---|---|---|---|---|---|---|---|
| 7 | HOCH$_2$C{CH$_2$OSi[OSi(sec. C$_4$H$_9$O)$_3$]$_2$CH$_3$}$_3$ | <−40 | 157.68 | 34.65 | 0.56 | 3.98 | 420 | 0.02 |

What is claimed is:

1. A compound having a formula selected from the following:

(a) 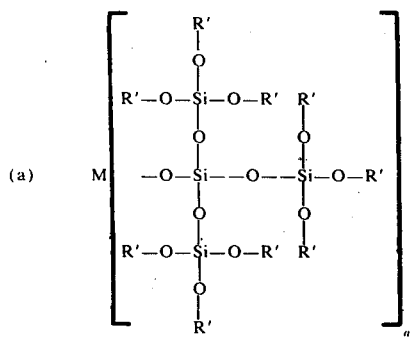

and (b) 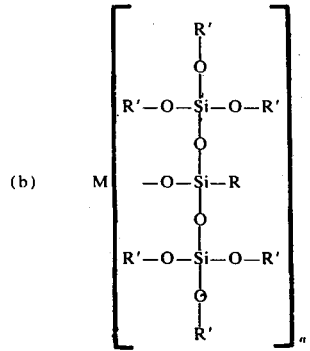

wherein $a = 2$, 3 or 4; M is a substituted or unsubstituted branched or straight chain hydrocarbon radical; R is hydrogen, an alkyl, alkenyl, aryl or aralkyl group and each R' is independently selected from the same group as R with the proviso that at least a majority of R' radicals are sterically hindered alkyl groups having at least 3 carbon atoms.

2. The compound of claim 1 wherein M is a substituted or unsubstituted branched or straight chain hydrocarbon radical which has been oxylated; R is hydrogen, an alkyl or alkenyl having about 1 to about 18 carbon atoms or an aryl or aralkyl having about 6 to about 24 carbon atoms, and each R' is independently selected from the same group as R, subject to the above proviso.

3. The compound of claim 2 wherein a majority of the R' radicals are sterically hindered alkyl groups having about 3 to about 24 carbon atoms.

4. The compound of claim 1 wherein $a = 2$ or 3; M has about 2 to about 18 carbon atoms; R is hydrogen, an alkyl having about 1 to about 8 carbon atoms or an aryl or aralkyl having about 6 to about 14 carbon atoms, and each R' is independently selected from the same group as R, subject to the above proviso.

5. The compound of claim 4 wherein M has about 4 to about 12 carbon atoms and a majority of the R' radicals are sterically hindered alkyl groups having about 4 to about 12 carbon atoms.

6. The compound of claim 1 wherein $a = 2$ or 3; M has about 2 to about 18 carbon atoms and a majority of the R' radicals are sterically hindered alkyl groups having about 3 to about 24 carbon atoms.

7. The compound of claim 6 wherein $a = 2$; M has about 4 to about 12 carbon atoms and a majority of the R' radicals are sterically hindered alkyl groups having about 4 to about 12 carbon atoms.

8. The compound of claim 1 wherein the compound is represented by the Formula (a).

9. The compound of claim 1 wherein the compound is represented by the Formula (b).

10. A method of preparing the compound of claim 1 comprising:
reacting a polyol having the formula M(OH)$_a$, wherein M and $a$ are defined above;
with about 0.5 to about 3 moles, per mole of equivalent of polyol, of a halogenated oxysilane starting material having a formula selected from the following:
c. XSi[OSi(OR')$_3$]$_3$
and
d. XSiR[OSi(OR')$_3$]$_2$
wherein X is a halogen selected from F, Cl, Br and I, and the other variables are defined above;
in the presence of about 0.7 to about 5 moles of a hydrogen halide acceptor base compound, per mole of halogenated oxysilane starting material;
said reaction being carried out at −30° C. to about the reflux temperature of the lowest boiling constituent in the reaction mixture.

11. The method of claim 10 wherein X is selected from Cl, Br and I.

12. The method of claim 10 wherein M is a substituted or unsubstituted branched or straight chain alkylene radical which has been oxylated; R is hydrogen, an alkyl or alkenyl having about 1 to about 18 carbon atoms or an aryl or aralkyl having about 6 to about 24 carbon atoms, and each R' is independently selected from the same gorup as R with the proviso that at least a majority of the R' radicals are sterically hindered alkyl groups having about 3 to about 24 carbon atoms.

13. The method of claim 12 wherein $a = 2$ or 3; M has about 2 to about 18 carbon atoms; R is hydrogen, an alkyl having about 1 to about 8 carbon atoms or an aryl or aralkyl having about 6 to about 14 carbon atoms, and each R' is independently selected from the same group as R, subject to the above proviso.

14. The method of claim 12 wherein $a = 2$; M has about 4 to about 12 carbon atoms; a majority of the R' radicals are sterically hindered alkyl groups having about 4 to about 12 carbon atoms, and X is Cl.

15. The method of claim 12 wherein about 1 to about 1.5 moles of the halogenated oxysilane starting material is used per equivalent of said polyol.

16. The method of claim 15 wherein about 0.9 to about 1.5 moles of the hydrogen halide acceptor base compound is used per mole of said halogenated oxysilane starting material.

17. The method of claim 16 wherein said reaction is carried out at 0° to 100° C.

18. The method of claim 10 wherein said starting material is represented by Formula (c).

19. The method of claim 10 wherein said starting material is represented by Formula (d).

* * * * *